(12) United States Patent
Cai et al.

(10) Patent No.: US 6,297,256 B1
(45) Date of Patent: Oct. 2, 2001

(54) ARYL AND HETEROARYL SUBSTITUTED PYRIDINO DERIVATIVES GABA BRAIN RECEPTOR LIGANDS

(75) Inventors: Guolin Cai, Guilford, CT (US); Gang Liu, Agoura, CA (US); Pamela A. Albaugh, Clinton, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/596,031

(22) Filed: Jun. 15, 2000

Related U.S. Application Data

(60) Provisional application No. 60/139,202, filed on Jun. 15, 1999.

(51) Int. Cl.[7] ............... G07D 401/04; A61K 31/44
(52) U.S. Cl. ............... 514/301; 514/300; 514/314; 514/340; 514/341; 546/113; 546/114; 546/176; 546/272.4; 546/272.7
(58) Field of Search ............... 546/113, 114, 546/176, 272.4, 272.7; 514/300, 301, 314, 340, 341

(56) References Cited

U.S. PATENT DOCUMENTS 4,560,692 * 12/1985 Field et al. ............... 514/313
4,728,647 * 3/1988 Benavides et al. ............... 514/222

* cited by examiner

Primary Examiner—Zinna Northington Davis
(74) Attorney, Agent, or Firm—McDonnell Boehnen Hulbert & Berghoff

(57) ABSTRACT

Disclosed are aryl and heteroaryl substitated pyridino compounds. These compounds are highly selective agonists, antagonists or inverse agonists for $GABA_A$ brain receptors or prodrugs of agonists, antagonists or inverse agonists for $GABA_A$ brain receptors and are therefore useful in the diagnosis and treatment of anxiety, depression, Down Syndrome, sleep and seizure disorders, overdose with benzodiazepine drugs and for enhancement of memory. Pharmaceutical compositions, including packaged pharmaceutical compositions, are further provided. Compounds of the invention are also useful as probes for the localization of $GABA_A$ receptors in tissue samples.

22 Claims, No Drawings

ARYL AND HETEROARYL SUBSTITUTED PYRIDINO DERIVATIVES GABA BRAIN RECEPTOR LIGANDS

This application claims priority to U.S. Provisional Application No. 60/139,202 filed Jun. 15, 1999 which is hereby incorporated by reference, in their entirety.

BACKGROUND OF THE INVENTION

1. Field of the Invention

This invention relates to aryl and heteroaryl substituted pyridino derivatives and to compounds that bind to the benzodiazepine site of $GABA_A$ receptors. This invention also relates to pharmaceutical compositions comprising such compounds and to the treatment of central nervous system (CNS) diseases.

2. Description of the Related Art

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits (Pritchett & Seeburg *Science* 1989; 245:1389–1392 and Knight et. al., *Recept. Channels* 1998; 6:1–18). Evidence such as message distribution, genome localization and biochemical study results suggest that the major naturally occurring receptor combinations are $α_1β_2γ_2$, $α_2β_3γ_2$, $α_3β_3γ_2$, and $α_5β_3γ_2$ (Mohler et. al. Neuroch. Res. 1995; 20(5): 631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, 6th ed., 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of other CNS active compounds. For example, there is evidence that selective serotonin reuptake inhibitors (SSRIs) may show greater antidepressant activity when used in combination with $GABA_A$ selective ligands than when used alone.

A variety of 2-aryl-4-piperidinoquinoline derivatives have been reported. See U.S. Pat. Nos. 4,560,692 and 4,728,647.

SUMMARY OF THE INVENTION

This invention provides heteroaryl substituted piperidines that bind with high affinity and high selectivity to the benzodiazepine site of the $GABA_A$ receptor, including human $GABA_A$ receptors.

Thus, the invention provides novel compounds of Formula I (shown below), and pharmaceutical compositions comprising compounds of Formula I.

The invention further comprises methods of treating patients suffering from CNS disorders with a therapeutically effective amount of a compound of the invention. The patient may be a human or other mammal. Treatment of humans, domesticated companion animals (pet) or livestock animals suffering from CNS disorders with an effective amount of a compound of the invention is encompassed by the invention.

In a separate aspect, the invention provides a method of potentiating the actions of other CNS active compounds. This method comprises administering an effective amount of a compound of the invention with another CNS active compound.

Additionally this invention relates to the use of the compounds of the invention as probes for the localization of $GABA_A$ receptors in tissue sections.

Accordingly, a broad aspect of the invention is directed to compounds of Formula I:

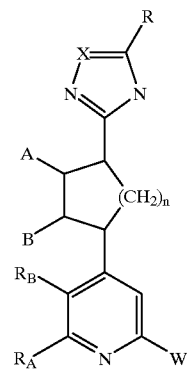

wherein:
n is 0 or an integer of from 1–3;
X is nitrogen or CR', where R' is lower hydrocarbyl or hydrogen;
R is hydrogen, lower hydrocarbyl, hydroxy, lower alkoxy, hydroxyhydrocarbyl, aminohydrocarbyl, or mono or di($C_1$–$C_6$ hydrocarbyl)aminohydrocarbyl;

A and B are the same or different and represent hydrogen, or straight or branched chain lower hydrocarbyl having 1–6 carbon atoms;

$R_A$ and $R_B$, together with the two carbon atoms to which they are attached, form a 5–7 membered aryl group, or a 5–7 membered saturated or unsaturated ring optionally containing 1 or 2 nitrogens, or a heteroaryl ring having 5–7 members and containing at least one nitrogen, wherein each ring may be optionally substituted with 1, 2, or 3 substituents independently selected from halogen, hydroxy, $C_1$–$C_6$ alkyl, alkoxy, amino, or mono or di($C_1$–$C_6$ alkyl)amino;

W is aryl or heteroaryl, each of which may be mono-, di- or trisubstituted independently with halogen, hydroxy, ($C_1$–$C_6$)lower hydrocarbyl, ($C_1$–$C_6$)lower alkoxy, amino, or mono- or di($C_1$–$C_6$)hydrocarbylamino.

DETAILED DESCRIPTION OF THE INVENTION

The novel compounds encompassed by the instant invention can be described by general Formula I set forth above or the pharmaceutically acceptable non-toxic salts thereof.

Preferred compounds of Formula I include those wherein:

n is 0 or an integer of from 1–3;

X is nitrogen or CR', where R' is lower alkyl or hydrogen;

R is hydrogen, lower alkyl, hydroxy, lower alkoxy, hydroxyalkyl, aminoalkyl, or mono or di($C_1$–$C_6$ alkyl) aminoalkyl;

A and B are the same or different and represent hydrogen, or $C_1$–$C_6$ alkyl having 1–6 carbon atoms;

$R_A$ and $R_B$, together with the two carbon atoms to which they are attached, form a 5–7 membered aryl group, or a 5–7 membered saturated or unsaturated ring optionally containing 1 or 2 nitrogens, or a heteroaryl ring having 5–7 members and containing at least one nitrogen, wherein each ring may be optionally substituted with 1, 2, or 3 substituents independently selected from halogen, hydroxy, $C_1$–$C_6$ alkyl, alkoxy, amino, or mono or di($C_1$–$C_6$ alkyl)amino;

W is aryl or heteroaryl, each of which may be mono-, di- or trisubstituted independently with halogen, hydroxy, ($C_1$–$C_6$)lower alkyl, ($C_1$–$C_6$)lower alkoxy, amino, or mono- or di($C_1$–$C_6$)alkylamino.

Preferred compounds of Formula I further include those where A and B are the same or different and represent hydrogen or methyl. Preferred compounds of Formula I include those where $R_A$ and $R_B$, together with the two carbon atoms to which they are attached, form a benzo, thieno, pyridino, or pyrimidino group. Each of these groups may be optionally substituted with 1, 2, or 3 substituents independently selected from halogen, hydroxy, $C_1$–$C_6$ alkyl, alkoxy, amino, or mono or di ($C_1$–$C_6$ alkyl)amino. Thus, more preferred compounds of Formula I include those where $R_A$ and $R_B$, together with the two carbon atoms to which they are attached, form a benzo, thieno, pyridino, or pyrimidino ring, each of which is optionally substituted with 1, 2, or 3 substituents independently selected from halogen, hydroxy, $C_1$–$C_6$ alkyl, alkoxy, amino, or mono or di($C_1$–$C_6$ alkyl) amino.

Preferred W substituents on compounds of the invention include phenyl, 2- or 3-thienyl, or 2-, 3-, or 4-pyridyl, each of which may be mono-, di- or trisubstituted independently with halogen, hydroxy, ($C_1$–$C_6$)lower alkyl, ($C_1$–$C_6$)lower alkoxy, amino, or mono- or di($C_1$–$C_6$)alkylamino. A particularly preferred W group is phenyl optionally substituted with halogen, hydroxy, ($C_1$–$C_6$)lower alkyl, ($C_1$–$C_6$)lower alkoxy, amino, or mono- or di($C_1$–$C_6$)alkylamino.

In addition, the present invention also encompasses compounds of Formula IIa and IIb:

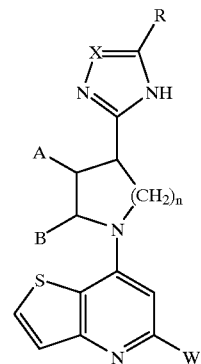

IIa

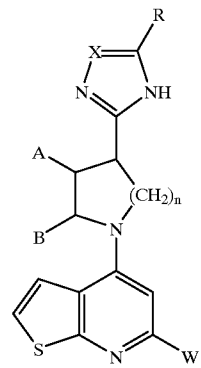

IIb wherein A, B, W, R, X and n are as defined above for Formula I.

Preferred compounds of Formula IIa and Formula IIb are where n is 2; A and B are independently hydrogen or methyl; and W is phenyl or 2-, 3-, or 4-pyridyl, each of which is optionally mono or disubstituted independently with halogen, hydroxy, lower alkyl or lower alkoxy.

The present invention also encompasses compounds of Formula IIIa and Formula IIIb:

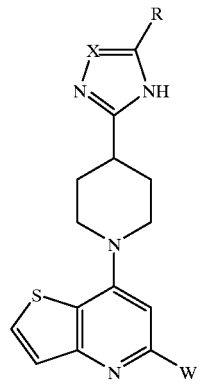

IIIa

-continued

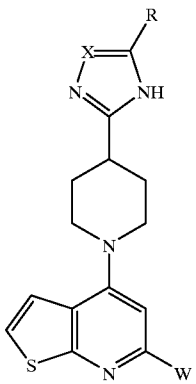

IIIb wherein W, R, and X are as defined above for Formula I.

Preferred compounds of Formula IIIa and Formula IIIb are where W is phenyl or 2-, 3-, or 4-pyridyl, each of which is optionally mono or disubstituted independently with halogen, hydroxy, lower alkyl or lower alkoxy.

The present invention also encompasses compounds of Formula IV:

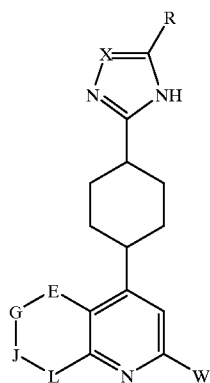

wherein W, X and R are as defined above in Formula I; and E, G, J, and L are independently nitrogen or $CR_1$, where $R_1$ is hydrogen, lower alkoxy, halogen, hydroxy, hydroxyalkyl, aminoalkyl, alkoxyalkyl, thio, or arylalkyl; provided that no more than two of E, G, J, and L are nitrogen.

Preferred compounds of Formula IV are where W is phenyl or 2-, 3-, or 4-pyridyl, each of which is optionally mono or disubstituted independently with halogen, hydroxyl, lower alkyl, or lower alkoxy.

The compounds of this invention may contain one or more chiral centers, e.g., asymmetric carbon atoms, so that the compounds can exist in different stereoisomeric forms. These compounds can be, for example, mixtures of diastereomers, or racemates or resolved enantiomers. Single enantiomers can be obtained as pure compounds or in enantiomeric excess by asymmetric synthesis or by resolution of the racemate. Resolution of the racemate can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid and base addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutically acceptable salts include, but are not limited to salts with inorganic acids such as hydrochloric, sulfuric, phosphoric, diphosphoric, hydrobromic, and nitric or salts with an organic acids such as formic, citric, malic, maleic, fumaric, tartaric, succinic, acetic, lactic, methanesulfonate, p-toluenesulfonate, 2-hydroxyethylsulfonate, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts as well as suitable methodologies for their preparation.

The present invention also encompasses prodrugs of the compounds of Formula I, e.g., acylated compounds and esters of Formula I. Those skilled in the art will recognize various synthetic methodologies which may be employed to prepare non-toxic pharmaceutically acceptable addition salts and prodrugs of the compounds encompassed by Formula I.

Representative compounds of the invention are shown in Table I.

TABLE I

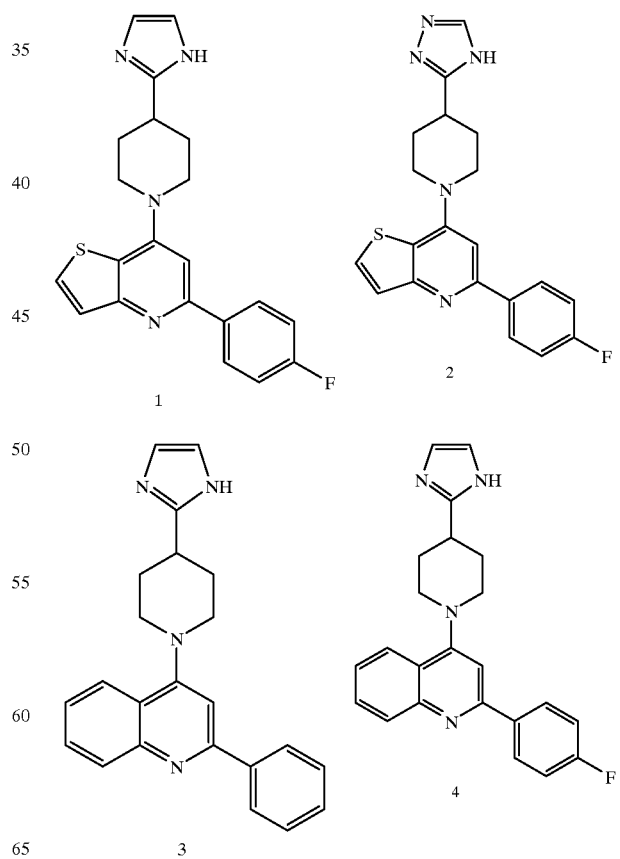

TABLE I-continued

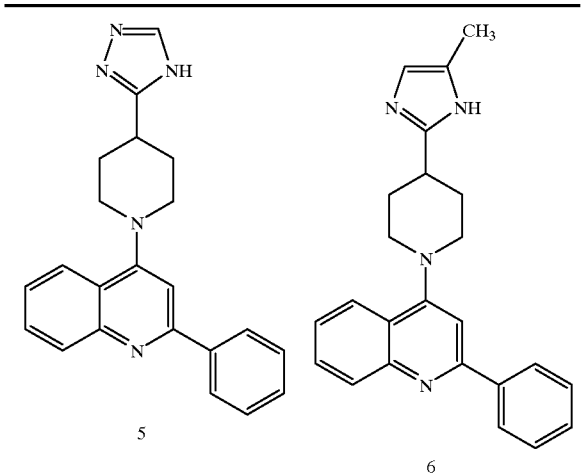

5

6

This invention provides compounds that bind with high affinity to the benzodiazepine site of $GABA_A$ receptors, including human $GABA_A$ receptors. This invention also provides compounds that bind with high selectivity to the benzodiazepine site of $GABA_A$ receptors, including human $GABA_A$ receptors. Without wishing to be bound by any particular theory, it is believed that the interaction of the compounds of Formula I with the benzodiazepine site results in the pharmaceutical utility of these compounds.

The invention further comprises methods of treating patients suffering from CNS disorders with an amount of a compound of the invention sufficient to alter the symptoms of the disorder. Compounds of the invention that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases, conditions and disorders that can be treated using compounds and compositions according to the invention include, but are not limited to, Depression, e.g. depression, atypical depression, bipolar disorder, depressed phase of bipolar disorder.

Anxiety, e.g. general anxiety disorder (GAD), agoraphobia, panic disorder+/−agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

The invention also provides pharmaceutical compositions comprising compounds of the invention. These compositions may be packaged pharmaceutical compositions for treating disorders responsive to $GABA_A$ receptor modulation, e.g., treatment of anxiety, depression, sleep disorders or cognitive impairment by $GABA_A$ receptor modulation. The packaged pharmaceutical compositions include a container holding a defined quantity or unit dose, e.g., a therapeutically effective amount, of at least one compound of the invention and instructions (e.g., labeling) indicating how the compound is to be used in the patient for treating a disorder that is, for example, responsive to $GABA_A$ receptor modulation.

In a separate aspect, the invention provides a method of potentiating the actions of other CNS active compounds, which comprises administering a therapeutically effective amount of a compound of the invention in combination with another CNS active compound. Such CNS active compounds include, but are not limited to the following: for anxiety, serotonin receptor (e.g. $5\text{-}HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the $GABA_A$ receptor ligand 3-(5-methylisoxazol-3-yl)-6-(1-methyl-1,2,3-triazol-4-yl) methyloxy-1,2,4-triazolo [3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The present invention also pertains to methods of inhibiting the binding of benzodiazepine compounds, such as Ro15-1788, to the $GABA_A$ receptors. These methods involve contacting a compound of the invention with cells expressing $GABA_A$ receptors, wherein the compound is present at a concentration sufficient to inhibit benzodiazepine binding to $GABA_A$ receptors in vitro. These methods include inhibiting the binding of benzodiazepine compounds to $GABA_A$ receptors in vivo, e.g., in a patient using an amount of a compound of Formula I that would be sufficient to inhibit the binding of benzodiazepine compounds to GABA$_A$ receptors in vitro. In one embodiment, such methods are useful in treating benzodiazepine drug overdose. The amount of a compound that would be sufficient to inhibit the binding of a benzodiazepine compound to the GABA$_A$ receptor may be readily determined via a GABA$_A$ receptor binding assay, such as the assay described in Example 9. The GABA$_A$ receptors used to determine in vitro binding may be obtained from a variety of sources, for example from preparations of rat cortex or from cells expressing cloned human GABA$_A$ receptors.

The present invention also pertains to methods for altering the signal-transducing activity, particularly the chloride ion conductance of GABA$_A$ receptors. These methods comprise exposing cells expressing such receptors to an effective amount of a compound of the invention. These methods include altering the signal-transducing activity of GABA$_A$ receptors in vivo, e.g., in a patient using an amount of a compound of Formula I that would be sufficient to alter the signal-transducing activity of GABA$_A$ receptors in vitro. The amount of a compound that would be sufficient to alter the signal-transducing activity of GABA$_A$ receptors may be determined via a GABA$_A$ receptor signal transduction assay, such as the assay described in Example 10.

The compounds of this invention and labeled derivatives thereof are also useful as standards and reagents in determining the ability of a potential pharmaceutical to bind to the GABA$_A$ receptor.

Radiolabeled derivatives of the compounds of the invention are also useful as radiotracers for positron emission tomography (PET) imaging or for single photon emission computerized tomography (SPECT).

Definitions

Where the compounds of the present invention have asymmetric centers, this invention includes all of the optical isomers and mixtures thereof.

Compounds with carbon-carbon double bonds may occur in Z- and E- forms, and all the isomers of the compounds of Formula I are included in the invention.

When any variable (e.g. $C_{1-6}$ alkyl, $C_{1-8}$ alkyl, W, R or X) occurs more than one time in any of the formulas herein, its definition at each occurrence is independent of its definition at every other occurrence.

By "$C_1$–$C_6$ alkyl" in the present invention is meant straight or branched chain alkyl groups having 1–6 carbon atoms. Examples of alkyl groups include, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_6$ alkyl groups are methyl, ethyl, propyl, butyl.

By "$C_1$–$C_6$ hydrocarbyl" and "lower hydrocarbyl" in the present invention is meant straight or branched chain alkyl groups having 1–6 carbon atoms, optionally containing one or more carbon-carbon double or triple bonds. $C_1$–$C_6$ hydrocarbyl includes $C_1$–$C_6$ alkyl, $C_2$–$C_6$ alkenyl, and $C_2$–$C_6$ alkynyl. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, 2-pentenyl, and propargyl. When reference is made herein to $C_1$–$C_6$ hydrocarbyl containing one or two double or triple bonds it is understood that at least two carbons are present in the alkyl for one double or triple bond, and at least four carbons for two double or triple bonds.

The term "alkoxy" represents an alkyl group of indicated number of carbon atoms attached to the parent molecular moiety through an oxygen bridge, such as methoxy, ethoxy, propoxy and isopropoxy. The term "lower alkoxy" includes alkyl groups of from 1 to 6 carbons atoms attached through an oxygen bridge.

By "aryl" is meant at least one aromatic ring optionally attached to one or more 5-, 6-, or 7-membered aromatic or nonaromatic rings, e.g., phenyl, 1,2,3,4-tetrahydronaphthalene and naphthyl.

The term "cycloalkylalkyl," as used herein, refers to a $C_3$–$C_7$ cycloalkyl group attached to the parent molecular moiety through an alkyl group, as defined above. Examples of cycloalkylalkyl groups include cyclopropylmethyl and cyclopentylethyl.

The term "halogen" indicates fluorine, chlorine, bromine, or iodine.

By "heteroaryl" is meant one or more aromatic ring systems of 5-, 6-, or 7-membered rings containing at least one and up to four heteroatoms selected from nitrogen, oxygen, or sulfur. Such heteroaryl groups include, thienyl, furanyl, pyrroyl, thiazolyl, imidazolyl, isoxazolyl, oxazolyl, pyridinyl, pyrimidinyl, isoquinolinyl, quinolinyl, napthyridinyl, benzimidazolyl, benzoxazolyl.

Pharmaceutical Preparations

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the compound or a composition containing the compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

Preparation of Compounds

An illustration of the preparation of compounds of the present invention is given in Schemes I and II. W, and R are as defined above for Formula I. Ring C represents $R_A$ and $R_B$ and the carbons to which they are attached.

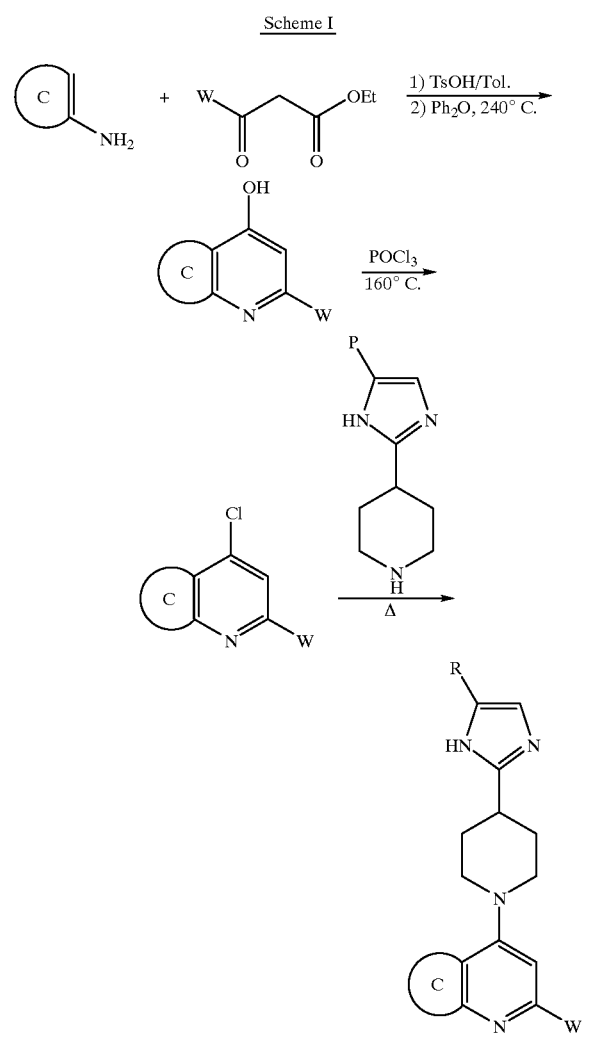

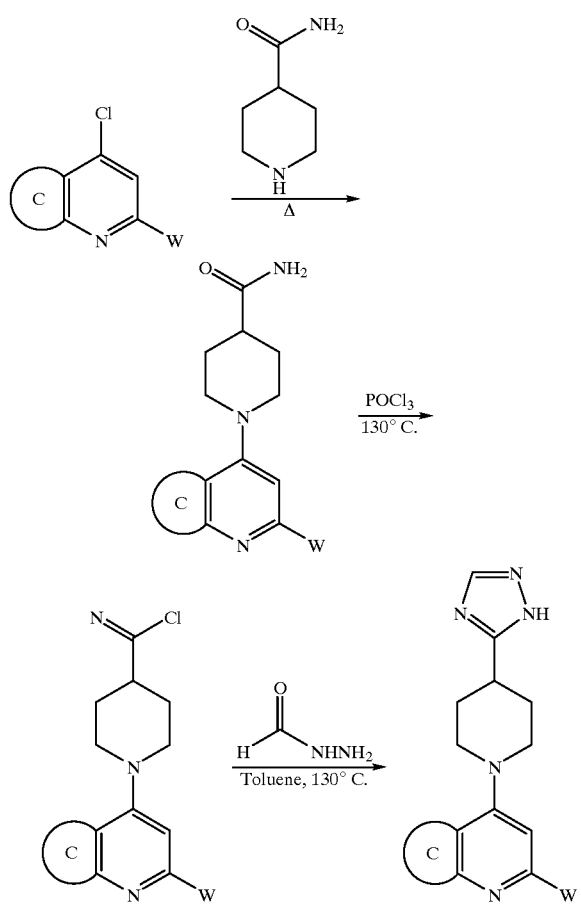

The disclosures in this application of all articles and references, including patents, are incorporated herein by reference.

The invention is illustrated further by the following examples, which are not to be construed as limiting the invention in scope or spirit to the specific procedures described in them. Those having skill in the art will recognize that the starting materials and reaction conditions may be varied, the order of the reactions may be altered, and additional reactions may be employed to produce compounds encompassed by the present inventions, as demonstrated by the following examples.

The starting materials used herein are either commercially available, known, or capable of being prepared by methods known in the art, i.e., literature methods. Further, those skilled in the art will recognize how to modify literature procedures to prepare desired starting materials. Unless otherwise specified all reagents and solvents are of standard commercial grade and are used without further purification. In some cases, protection of reactive functionalities may be necessary to achieve some of the desired transformations. In general, such need for protecting groups, as well as the conditions necessary to attach and remove such groups, will be apparent to those skilled in the art of organic synthesis.

EXAMPLE 1

5-(4-Fluorophenyl)-thieno[3,2-b]pyridin-7-ol

A mixture of 3-amino-2-thiophenecarboxylic acid (8 g, 49 mmol), ethyl 4-fluorobenzoylacetate (9.6 g, 49 mmol), and p-toluenesulfonic acid monohydrate (0.2 g, 1 mmol) in toluene (100 mL) is refluxed for about 20 hours in a flask equipped with a Dean-Stark water trap. The mixture is cooled to room temperature. The precipitate is filtered and washed with diethyl ether. The solid is dissolved in diphenyl ether (80 mL) and heated at 240° C. for about 2 hours. The reaction solution is then cooled to room temperature, diethyl ether is added and the precipitate is filtered and washed with diethyl ether to give 5-(4-fluorophenyl)-thieno[3,2-b] pyridin-7-ol (2 g, 17% yield) as brown crystalline needles, m.p. 316–318 ° C.

EXAMPLE 2

7-Chloro-5-(4-fluorophenyl)thieno[3,2-b]pyridine

A solution of 5-(4-fluorophenyl)-thieno[3,2-b]pyridin-7-ol (1.6 g) in phosphorus oxychloride (50 mL) is refluxed for 3 hours. After the excess phosphorus oxychloride is removed under vacuum, the residue is treated with ethyl acetate (20 mL), and NaOH (2N, 20 mL). The mixture is then extracted with ethyl acetate (3×20 mL). The combined organic layers are washed with brine, dried over MgSO$_4$, and filtered. Evaporation of the solvent gives 7-chloro-5-(4-fluorophenyl)thieno[3,2-b]pyridine (1.5 g, 88% yield) as a white solid, m.p. 119–121° C.

EXAMPLE 3

5-(4-fluorophenyl)-7-(4-imidazol-2-ylpiperidyl) thioipheno[3,2-b]pyridine

A mixture of 7-chloro-5-(4-fluorophenyl)thieno[3,2-b] pyridine (146 mg, 0.53 mmol), 4-(1H-imidazol-2-yl) piperidine. hydrochloride (U.S. Pat. No. 4,431,653) (100 mg, 0.53 mmole) and sodium acetate (50 mg) in ethylene glycol (10 mL) is stirred and heated at 160° C. for about 16 hours. It is then cooled, diluted with ethylacetate (15 mL), and washed with water (3×15 mL). The organic layer is dried over sodium sulfate, filtered, and concentrated. The residue is purified by preparative thin layer chromatography to give 5-(4-fluorophenyl)-7-(4-imidazol-2-ylpiperidyl) thiopheno[3,2-b]pyridine (36 mg, 18% yield) as a white solid, m.p. 95° C. (compound 1).

EXAMPLE 4

1-(5-(4-Fluorophenyl)thieno[3,2-b]pyridin-7-yl) pireridine-4-carboxamide

A mixture of 7-chloro-5-(4-fluorophenyl)thieno[3,2-b] pyridine (68 mg, 0.26 mmole), isonipecotamide (66 mg, 0.52 mmole), and sodium acetate (21 mg, 0.26 mmole) in 1-methyl-2-pyrrolidone (3 mL) is stirred and heated in an oil bath at 160° C. for about 4 hours. The reaction mixture is then cooled, diluted with ethyl acetate (15 mL) and washed with water (3× 15 mL). The organic layer is dried over sodium sulfate, filtered, and concentrated. The residue is recrystalized with ethyl acetate to give 1-(5-(4-fluorophenyl)thieno[3,2-b]pyridin-7-yl)piperidine-4-carboxamide (55 mg, 60% yield) as a white solid product (m.p. 251° C.–253° C.).

EXAMPLE 5

5-(4-Fluorophenyl)-7-[4-(4H-1,2,4-triazol-3-yl) piperidyl]thioheno[3,2-b]pyridine A suspension of 1-(5-(4-fluorophenyl)thieno[3,2-b] pyridin-7-yl)piperidine-4-carboxamide (100 mg, 0.32 mmole) in phosphorus oxochloride (5 mL) is refluxed for about 30 minutes. After the excess phosphorus oxychloride is removed under vacuum, the residue is treated with ethyl acetate (5 mL), and ice-water (10 mL). The mixture is extracted with ethyl acetate (3×10 mL). The combined organic layers are washed with brine, dried over sodium fate, filtered, and concentrated. The residue is dissolved in toluene (5 mL) and then formic hydrazide (100 mg, 1.7 mmole) and formic acid (0.05 mL) are added. The reaction mixture is refluxed for about 16 hours. It is then cooled, diluted with ethyl acetate (15 mL), and washed with water (3×15 mL). The organic layer is dried over sodium sulfate, filtered, and concentrated. The residue is purified by preparative tlc to give 5-(4-fluorophenyl)-7-[4-(1H-1,2,4-triazol-3-yl)-1-piperidinyl]thieno[3,2-b]pyridine (7 mg, 6% yield) as a white solid. This material is dissolved in ethyl acetate (1 mL), saturated with HCl (2 mL), and then concentrated to afford 5-(4-Fluorophenyl)-7-[4-(4H-1,2,4-triazol-3-yl) piperidyl]thioheno[3,2-b]pyridine hydrochloride (compound 2) as greasy oil. Trituration with ether, filtration and drying in vacuo affords the desired product as a solid. m.p. >300° C. (dec).

EXAMPLE 6

The following compounds are prepared essentially according to the procedure described in Examples 1–5:

a) 2-[1-(2-phenyl-4-quinolyl)-4-piperidyl]imidazole (compound 3), m.p. >310° C. (dec);

b) 2-{1-[2-(4-fluorophenyl)-4-quinolyl]-4-piperidyl}imidazole hydrochloride (compound 4), m.p. >310° C. (dec);

c) 3-[1-(2-phenyl-4-quinolyl)-4-piperidyl]-4H-1,2,4-triazole hydrochloride (compound 5), m.p. >240° C. (dec);

d) 5-methyl-2-[1-(2-phenyl-4-quinolyl)-4-piperidyl] imidazole hydrochloride (compound 6), m.p. >300° C. (dec).

EXAMPLE 7

Preparation of Radiolabeled Probe Compounds of the Invention

The compounds of the invention can be prepared as radiolabeled probes by carrying out their synthesis using precursors comprising at least one atom that is a radioisotope. The radioisotope is preferably selected from of at least one of carbon (preferably $^{14}$C), hydrogen (preferably $^{3}$H), sulfur (preferably 35S), or iodine (preferably $^{125}$I). Such radiolabeled probes are conveniently synthesized by a radio-isotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Ks.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Tritium labeled probe compounds can also be prepared, when appropriate, by sodium borotritide reduction. Such preparations are also conveniently carried out as a custom radiolabeling by any of the suppliers listed in the preceding paragraph using the compound of the invention as substrate.

EXAMPLE 7A

Preparation of Radiolabeled Compounds of Formula

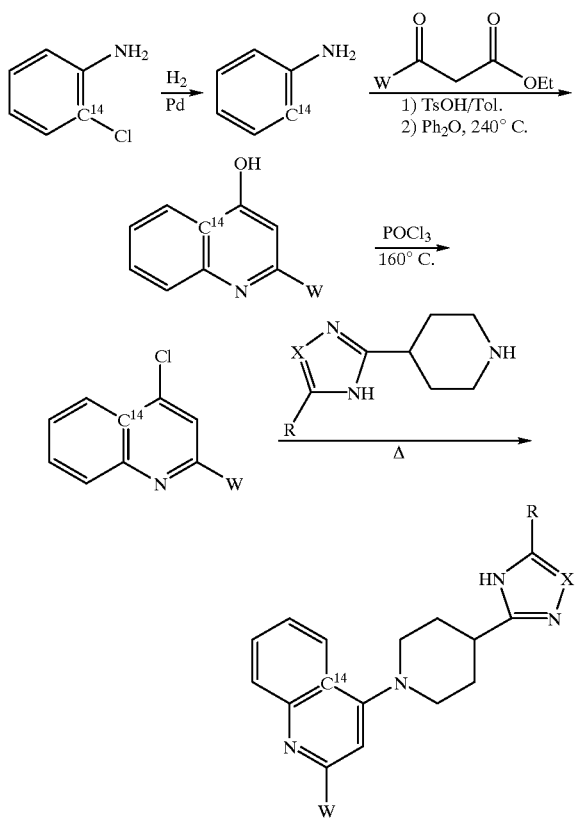

The above scheme, a modification of Scheme I, represents a method for preparation of radiolabeled probe compounds of the invention. This synthesis is carried out using ARC-365 aniline hydrochloride [$^{14}$C(U)], supplied by American Radiolabeled Chemicals, Inc., St. Louis, Mo., as the radioisotope precursor.

EXAMPLE 8

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

EXAMPLE 9

Binding Assay

The following assay is used for determining $GABA_A$ binding affinity. The high affinity and high selectivity of compounds of this invention for the benzodiazepine site of the $GABA_A$ receptor is confirmed using the binding assay described in Thomas and Tallman (*J. Bio. Chem.* 1981; 156:9838–9842, and *J. Neurosci.* 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of fresh buffer, and recentrifuged at 20,000×g. The supernatant of this centrifugation step is decanted and the pellet stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations containing 100 μl of tissue homogenate, 100 μl of radioligand, (0.5 nM $^3$H-Ro15-1788 [$^3$H-Flumazenil], specific activity 80 Ci/mmol), and test compound or control (see below), and are brought to a total volume of 500 μl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^3$H Ro15-1788 with 10 μM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve is obtained with up to 11 points spanning the compound concentration range from $10^{-2}$M to $10^{-5}$M obtained per curve by the method described above for determining percent inhibition. $K_i$ values are calculated according the Cheng-Prussof equation. When tested in this assay, compounds of the invention exhibit $K_i$ values of less than 1 μM, preferred compounds of the invention have $K_i$ values of less than 500 nM and more preferred compounds of the invention have $K_i$ values of less than 100 nM.

EXAMPLE 10

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. *Xenopus laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_5\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human β2, GENBANK accession no. M82919; human β3, GENBANK accession no. Z20136; human $\beta_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 μM GABA is applied.

Compounds are evaluated against a GABA concentration that evokes <10% of the maximal evokable GABA current (e.g. 1 $\mu$M–9 $\mu$M). Each oocyte is exposed to increasing concentrations of compound in order to evaluate a concentration/effect relationship. Compound efficacy is calculated as a percent-change in current amplitude: 100*((Ic/I)–1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 $\mu$M RO15-1788, followed by exposure to GABA+1 $\mu$M RO15-1788+test compound. Percent change due to addition of compound is calculated as described above. Any percent change observed in the presence of RO15-1788 is subtracted from the percent changes in current amplitude observed in the absence of 1 $\mu$M RO15-1788. These net values are used for the calculation of average efficacy and $EC_{50}$ values by standard methods. To evaluate average efficacy and $EC_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of Formula I:

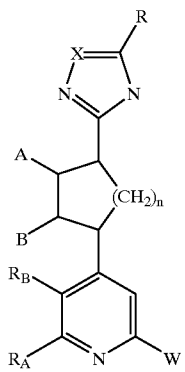

or a pharmaceutically acceptable non-toxic salt thereof, wherein:

n is 0 or an integer of from 1–3;

X is nitrogen or CR', where R' is lower hydrocarbyl or hydrogen;

R is hydrogen, lower hydrocarbyl, hydroxy, lower alkoxy, hydroxyhydrocarbyl, aminohydrocarbyl, or mono or di($C_1$–$C_6$ hydrocarbyl)aminohydrocarbyl;

A and B are the same or different and represent hydrogen, or straight or branched chain lower hydrocarbyl having 1–6 carbon atoms;

$R_A$ and $R_B$, together with the two carbon atoms to which they are attached, form a 5–7 membered aryl group, or a 5–7 membered saturated or unsaturated ring optionally containing 1 or 2 nitrogens, or a heteroaryl ring having 5–7 members and containing at least one nitrogen, wherein each ring may be optionally substituted with 1, 2, or 3 substituents independently selected from halogen, hydroxy, $C_1$–$C_6$ alkyl, alkoxy, amino, or mono or di($C_1$–$C_6$ alkyl)amino;

W is aryl, heteroaryl, 2- or 3-thienyl, or 2-, 3-, or 4-pyridyl, each of which may be mono-, di- or trisubstituted independently with halogen, hydroxy, ($C_1$–$C_6$) lower hydrocarbyl, ($C_1$–$C_6$)lower alkoxy, amino, or mono- or di ($C_1$–$C_6$)hydrocarbylamino.

2. A compound of Formula I:

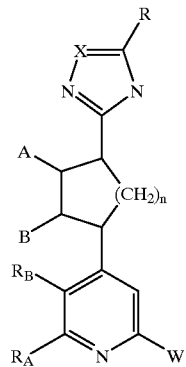

or a pharmaceutically acceptable non-toxic salt thereof, wherein:

n is 0 or an integer of from 1–3;

X is nitrogen or CR', where R' is lower alkyl or hydrogen;

R is hydrogen, lower alkyl, hydroxy, lower alkoxy, hydroxyalkyl, aminoalkyl, or mono or di($C_1$–$C_6$ alkyl) aminoalkyl;

A and B are the same or different and represent hydrogen, or straight or branched chain lower alkyl having 1–6 carbon atoms;

$R_A$ and $R_B$, together with the two carbon atoms to which they are attached, form a 5–7 membered aryl group, or a 5–7 membered saturated or unsaturated ring optionally containing 1 or 2 nitrogens, or a heteroaryl ring having 5–7 members and containing at least one nitrogen, wherein each ring may be optionally substituted with 1, 2, or 3 substituents independently selected from halogen, hydroxy, $C_1$–$C_6$ alkyl, alkoxy, amino, or mono or di($C_1$–$C_6$ alkyl)amino;

W is aryl or heteroaryl, 2- or 3-thienyl, or 2-, 3-, or 4-pyridyl, each of which may be mono-, di- or trisubstituted independently with halogen, hydroxy, ($C_1$–$C_6$) lower alkyl, ($C_1$–$C_6$)lower alkoxy, amino, or mono- or di($C_1$–$C_6$)alkylamino.

3. A compound according to claim 1 which is:

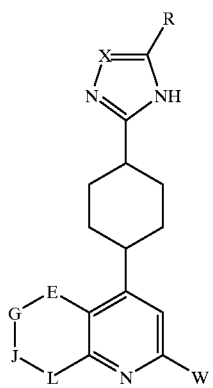

wherein
R is hydrogen, lower alkyl, hydroxy, lower alkoxy, hydroxyalkyl, or aminoalkyl; and
W is aryl or heteroaryl, each of which may be mono-, di- or trisubstituted independently with halogen, hydroxy, straight or branched chain lower alkyl having 1–6 carbon atoms, straight or branched chain lower alkoxy having 1–6 carbon atoms, amino, or mono- or dialkylamino where each alkyl portion is straight or branched chain lower alkyl having 1–6 carbon atoms;
X is CH or nitrogen; and
E, G, J, and L are independently nitrogen or $CR_1$, where $R_1$ is hydrogen, lower alkoxy, halogen, hydroxy, hydroxyalkyl, aminoalkyl, alkoxyalkyl, thio, or arylalkyl; provided that no more than two of E, G, J, and L are nitrogen.

4. A compound according to claim 1 which is 2-[1-(2-phenyl-4-quinolyl)-4-piperidyl]imidazole.

5. A compound according to claim 1 which is 2-{1-[2-(4-fluorophenyl)-4-quinolyl]-4-piperidyl}imidazole.

6. A compound according to claim 1 which is 3-[1-(2-phenyl-4-quinolyl)-4-piperidyl]-4H-1,2,4-triazole.

7. A compound according to claim 1 which is 5-methyl-2-[1-(2-phenyl-4-quinolyl)-4-piperidyl]imidazole.

8. A compound of the formula:

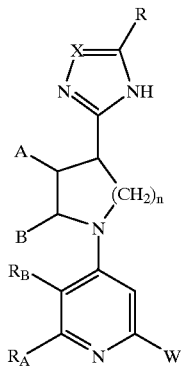

or a pharmaceutically acceptable salt thereof, wherein:

n is 0 or an integer of from 1–3;
X is nitrogen or CR', where R' is lower hydrocarbyl or hydrogen;
R is hydrogen, lower hydrocarbyl, hydroxy, lower alkoxy, hydroxyhydrocarbyl, aminohydrocarbyl, or mono or di($C_1$–$C_6$ hydrocarbyl)aminohydrocarbyl;
A and B are the same or different and represent hydrogen, or straight or branched chain lower hydrocarbyl having 1–6 carbon atoms;
$R_A$ and $R_B$, together with the two carbon atoms to which they are attached, form a thieno group which is optionally substituted with 1, 2, or 3 substituents independently selected from halogen, hydroxy, $C_1$–$C_6$ alkyl, alkoxy, amino, or mono or di($C_1$–$C_6$ alkyl)amino; and
W is aryl, heteroaryl, 2- or 3-thienyl, or 2-, 3-, or 4-pyridyl, each of which may be mono-, di- or trisubstituted independently with halogen, hydroxy, ($C_1$–$C_6$) lower hydrocarbyl, ($C_1$–$C_6$)lower alkoxy, amino, or mono- or di($C_1$–$C_6$)hydrocarbylamino.

9. A compound according to claim 8 which is:

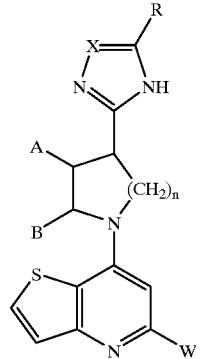

wherein:
X is CH or nitrogen.

10. A compound according to claim 8 which is:

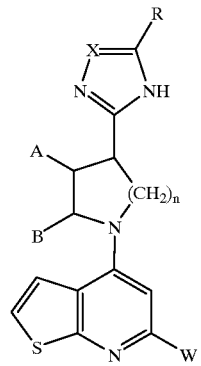

wherein:
X is CH or nitrogen.

11. A compound according to claim 8 which is:

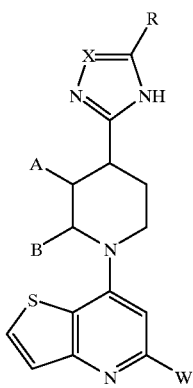

wherein:
X is CH or nitrogen;
R is hydrogen, lower alkyl, hydroxy, lower alkoxy, hydroxyalkyl, or aminoalkyl; and
W is aryl, heteroaryl, 2- or 3-thienyl, or 2-, 3-, or 4-pyridyl, each of which may be mono-, di- or trisubstituted independently with halogen, hydroxy, straight or branched chain lower alkyl having 1–6 carbon atoms, straight or branched chain lower alkoxy having 1–6 carbon atoms, amino, or mono- or dialkylamino where each alkyl portion is straight or branched chain lower alkyl having 1–6 carbon atoms.

12. A compound according to claim 9 which is:

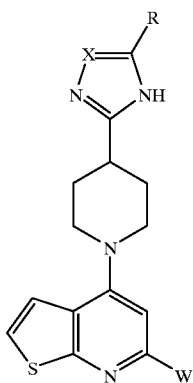

wherein:
X is CH or nitrogen;
R is hydrogen, lower alkyl, hydroxy, lower alkoxy, hydroxyalkyl, or aminoalkyl; and
W is phenyl, 2- or 3-thienyl, or 2-, 3-, or 4-pyridyl, each of which may be mono-, di- or trisubstituted independently with halogen, hydroxy, ($C_1$–$C_6$) lower alkyl, ($C_1$–$C_6$) lower alkoxy, amino, or mono- or di($C_1$–$C_6$) alkylamino.

13. A compound according to claim 11 which is 5-(4-fluorophenyl)-7-(4-imidazol-2-ylpiperidyl)thiopheno[3,2-b]pyridine.

14. A compound according to claim 11 which is 5-(4-fluorophenyl)-7-[4-(4H-1,2,4-triazol-3-yl)piperidyl]thiophens[3,2-b]pyridine.

15. A pharmaceutical composition comprising a compound according to claim 1 combined with at least one pharmaceutically acceptable carrier or excipient.

16. A method for the treatment of a disease or disorder associated with pathogenic agonism, inverse agonism or antagonism of the $GABA_A$ receptor, said method comprising administering to a patient in need of such treatment or prevention a therapeutically effective amount of a compound of claim 1.

17. A method according to claim 15 wherein the disease or disorder associated with pathogenic agonism, inverse agonism or antagonism of the $GABA_A$ receptor is anxiety, depression, a sleep disorder, or cognitive impairment.

18. A method for localizing $GABA_A$ receptors in a tissue sample comprising:
contacting with the sample a detectably-labeled compound of claim 1 under conditions that permit binding of the compound to $GABA_A$ receptors, washing the sample to remove unbound compound, and detecting the bound compound.

19. A method of inhibiting the binding of a benzodiazepine compound to a $GABA_A$ receptor, said method comprising contacting a compound of claim 1 with cells expressing such a receptor in the presence of the benzodiazepine, wherein the compound is present at a concentration sufficient to inhibit the binding a benzodiazepine compound to a $GABA_A$ receptor in vitro.

20. A method for altering the signal-transducing activity of $GABA_A$ receptors, said method comprising exposing cells expressing such receptors to a compound according to claim 1 at a concentration sufficient to inhibit RO15-1788 binding to cells expressing a cloned human $GABA_A$ receptor in vitro.

21. A packaged pharmaceutical composition comprising the pharmaceutical composition of claim 8 in a container and instructions for using the composition to treat a patient suffering from a disorder responsive to agonism, inverse agonism or antagonism of the $GABA_A$ receptor.

22. The packaged pharmaceutical composition of claim 21, wherein said patient is suffering from anxiety, depression, a sleep disorder, or cognitive impairment.

* * * * *